United States Patent [19]

Hoogenraad

[11] Patent Number: 6,064,073
[45] Date of Patent: May 16, 2000

[54] METHOD OF LOCALIZING AN OBJECT IN A TURBID MEDIUM

[75] Inventor: Johannes H. Hoogenraad, Eindhoven, Netherlands

[73] Assignee: U.S. Philips Corporation, New York, N.Y.

[21] Appl. No.: 09/115,786

[22] Filed: Jul. 14, 1998

[30] Foreign Application Priority Data

Jul. 15, 1997 [EP] European Pat. Off. ............... 97202187

[51] Int. Cl.[7] .............................. G01N 15/06; G06K 9/00
[52] U.S. Cl. .......................... 250/573; 382/128; 600/309
[58] Field of Search .................................... 250/573, 574, 250/575, 559.07, 559.2, 341.1; 382/128, 131, 132; 600/309, 310, 313, 425

[56] References Cited

U.S. PATENT DOCUMENTS 5,309,912  5/1994  Knuttel .................................... 600/425

FOREIGN PATENT DOCUMENTS 8912223  12/1989  WIPO .

OTHER PUBLICATIONS

"The forward and inverse problems in time resolved infra-red imaging", by S.R. Arridge, as published in Medical Optical Tomography, No. IS11, 1993, pp. 35–64.

"Algorithm for computer control of a digital plotter", by J.E. Bresenham, published in IBM Systems Journal, vol. 4, No. 1965, pp. 28–30.

*Primary Examiner*—John R. Lee
*Assistant Examiner*—Kevin Pyo
*Attorney, Agent, or Firm*—Dwight H. Renfrew

[57] ABSTRACT

The invention relates to a method of localizing an object in a turbid medium, utilizing an exponential function which determines the effect of an attenuation coefficient of a voxel of the turbid medium on an intensity of light transported through the turbid medium. In order to determine the estimated intensity variation on a photodetector, for each voxel the contribution to the intensity variation is determined by means of this exponential function. In order to reduce the required calculation time, this exponential function is approximated by a function which can be split into two orthogonal vectors. Consequently, the number of times that the value of an exponential function must be determined can be substantially reduced, resulting in a substantial reduction of the calculation time required for the reconstruction of an image of the interior of the turbid medium.

11 Claims, 3 Drawing Sheets

METHOD OF LOCALIZING AN OBJECT IN A TURBID MEDIUM

BACKGROUND OF THE INVENTION

1. Field of the Invention

The invention relates to a method of localizing an object in a turbid medium, which method includes the following steps:

irradiating the turbid medium and determining an intensity of a part of the light transported through the turbid medium along a plurality of light paths, from source points at which the light enters the turbid medium, to detector points at which the light leaves the turbid medium determining an estimated intensity of the light of a selected light path by way of a first combination of predetermined attenuation coefficients of voxels of the turbid medium and a predetermined weighting function which is related to a position of a voxel relative to the selected light path, determining a difference between an estimated intensity and the determined intensity for the selected light path, and determining a next value of the attenuation coefficients of the voxels by way of a second combination of the differences determined for the plurality of light paths.

The invention also relates to a device for carrying out a method of this kind.

2. Description of the Related Art

In the context of the present application the term light is to be understood to mean electromagnetic radiation of a wavelength in the range of from 400 to 1400 nm. Furthermore, a turbid medium is to be understood to mean a substance consisting of a material having a high light scattering coefficient. Examples in this respect are an Intralipid solution or biological tissue. Furthermore, an attenuation coefficient is to be understood to mean the inverse diffuse absorption distance $\kappa$.

A method of this kind is known from the article "The forward and inverse problems in time resolved infra-red imaging", by S. R. Arridge, as published in Medical Optical Tomography, No. IS11, 1993, pp. 35–64. The known iterative method of imaging the interior of the turbid medium is based on a three-dimensional set of attenuation coefficients $\kappa$ which correspond to the voxels of the turbid medium. Subsequently, for the respective light paths the estimated intensity is determined as the sum of the contributions of the change in intensity due to the predetermined attenuation coefficient of the voxels of the turbid medium. Subsequently, a difference set is determined from the estimated intensities and the measured intensities. Using the second combinations of the values of the difference set, corrections are determined for the attenuation coefficients $\kappa$ of the three-dimensional set.

After several iterations, the values of the attenuation coefficients $\kappa$ have converged and the values of the attenuation coefficient which correspond to different voxels in a plane can be represented in an image. The change of the estimated intensity dI of a selected light path due to a change $\Delta\kappa$ of the attenuation coefficient $\kappa$ of a volume element V is given by the formula:

$$-\frac{dI}{I} = \frac{\Delta\kappa V \kappa_0}{2\pi} \frac{|sd|}{|sp| \times |pd|} \exp[-\kappa_0(|sp| + |pd| - |sd|)] \quad (1)$$

in which $|sd|$ is the length of the selected light path, $|sp|$ is the distance between a measuring light source and the voxel, and $|pd|$ is the distance between the voxel and a photodetector opening. The formula (1) can subsequently be approximated by a product of a first function $W(x_{s,K})$ and the weighting function $W(x_{S,\rho,K})$, where K equals the product of the attenuation coefficient $\kappa$ and the selected light path $|sd|$ which is equal to the distance between the measuring light source and a photodetector opening. Furthermore, $\kappa$ is determined by $\kappa=\sqrt{3}\mu\mu_a\mu_s$ in which $\mu_a$ represents the absorption coefficient and $\mu_s'$ is the transport coefficient or the reduced scatter coefficient. The function $W(x_s,K)$ is determined by $$\frac{\Delta K V K_0}{2\pi(1-x_s)x_s} \quad (2)$$

In the diffusion approximation for infinite media, the weighting function $W(x_s,\rho, K)$ can be approximated by the formule $$W(x_s, \rho, K) = \frac{\sqrt{(1-x_s)^2 x_s^2}}{(\rho^2 + (1-x_s)^2(\rho^2 + x_s^2))} e^{-K\left(\sqrt{\rho^2 + (1-x_s)^2} + \sqrt{\rho^2 + x_s^2}\right) - 1} \quad (3)$$

in which $x_s$ is the distance between the light source and the shortest connecting line between the voxel and the selected light path and $\rho$ is the distance between the voxel and the selected light path, both said distances being normalized to the length of the selected shortest light path.

It is a drawback of the known method that the last formule (3) contains an exponential function and must be calculated separately for each voxel and for each light path through the turbid medium; these operations are comparatively time-consuming.

SUMMARY OF THE INVENTION

It is an object of the invention to reduce the calculation time required for the reconstruction. To this end, the method is characterized in that the weighting function is determined in such a manner that it contains a function which can be factorized to a first and a second orthogonal vector which extend transversely of the selected light path. The invention is based on the idea that the use of such an approximation of the weighting function enables a reduction of the number of calculations of exponential functions, thus reducing the overall calculation time required for the reconstruction. Further advantage is that reconstruction utilizing the factorizable function as an approximation of the formule (3) yields an image of the interior of the turbid medium which can possibly be used for medical diagnosis. For example, it can be used for in vivo detection of tumors in human or animal tissue.

It is a further advantage that a laboratory assistant has the image available comparatively soon after the intensity measurements. The saving as regards calculation time can be explained, for example on the basis of a plane containing N×N points for which a function value of an exponential function must be determined $N^2$ times. When the function contains a factorizable function, it suffices to determine 2N function values of the factorizable function and the function value of each point can be determined by a combination of the function values which have been determined in advance and stored in tables.

A special version of the method according to the invention is characterized in that the method also includes the following steps for determining the estimated intensity for the selected light path:

selecting a first axis of an orthogonal system which corresponds best to the direction of the selected light path, approximating the selected light path in the turbid medium by light path voxels, determining a plane perpendicular to the selected light path, said perpendicular plane being determined by a light path voxel and the first and the second orthogonal vector, approximating a first auxiliary line in the perpendicular plane which is oriented substantially parallel to the first orthogonal vector through first voxels, determining a table of a function W(s), dependent on the first vector, whose elements contain contributions of W(s) which are dependent on the distance between a first voxel and the selected light path, determining a partial sum of the estimated intensity of contributions by various first voxels as a product of a function W(t) which is dependent on the second orthogonal vector and elements of W(s). The first axis is chosen in such a manner that, relative to the two other axes of the orthogonal system, it is situated nearest to the selected light path. The number of calculations of an exponential function can thus be reduced by precalculation of W(t) along the first auxiliary line. The contribution to the estimated intensity of a selected light path for a plurality of voxels contained in the normal plane is subsequently determined, for example as the product of W(s) and an interpolated value of W(t). The interpolated value of W(t) is determined, for example by a zero-order or first-order interpolation. The contribution of substantially all voxels of the perpendicular plane to the estimated intensity of the selected light path can be determined by repeating this step, without it being necessary to calculate an exponential function for each voxel. In order to determine the estimated intensity associated with the selected light path, the contributions of substantially all voxels in the turbid medium is determined by successively determining the partial sums of the voxels of successive perpendicular planes which are situated along the selected light path and contain respective, successive light path voxels.

A further version of a method according to the invention is characterized in that for the approximation of the first auxiliary line two neighboring first voxels are determined in such a manner that associated co-ordinates differ by one grid unit in a direction of a second axis of the orthogonal system which is situated nearest to the first orthogonal vector. In the context of the present application a grid unit is to be understood to mean a unit along one of the three axes of the orthogonal system. An approximation of the first auxiliary line is obtained, for example by application of a Bresenham-like algorithm in which the co-ordinate in the axis situated nearest to the direction of the first auxiliary line always differs by one grid unit and the co-ordinates in the direction of the other axes are varied by one grid unit from time to time so as to follow the first auxiliary line. A Bresenham algorithm is known from the article "Algorithm for computer control of a digital plotter", by J. E. Bresenham, published in IBM Systems Journal, Vol. 4, No. 1965, pp. 28–30. The cited article describes an algorithm for approximating a line by way of grid points in an orthogonal grid, the line thus being approximated by line segments which interconnect the grid points; no divisions or multiplications are required so as to determine the co-ordinates and nevertheless efficiency is achieved in respect of processing speed and use of memory capacity.

A further version of a method is characterized in that the method includes a step in which a second auxiliary line in the perpendicular plane, being oriented substantially parallel to the first auxiliary line, is approximated by second voxels in such a manner that, in a direction of a third axis of the orthogonal system, co-ordinates of the second voxels differ by one grid unit from corresponding co-ordinates of the first voxels, the partial sum of the estimated intensity being determined for the contribution by different second voxels. The calculation time required to determine the co-ordinates of the other voxels in the perpendicular plane can be reduced by repeating this step.

A next version of a method is characterized in that for the approximation of the selected light path co-ordinates of two neighboring light path voxels differ by one grid unit in a direction of the first axis. An approximation of the selected light path by the light path voxels again is, for example a Bresenham algorithm where the co-ordinate in the axis situated nearest to the direction of the selected light path always differs by one grid unit and the co-ordinates in the direction of the other axes are changed by one grid unit from time to time so as to approximate the selected light path. The contribution by substantially all voxels of the turbid medium to the estimated intensity can thus be simply determined.

Another version of a method is characterized in that the first or the second orthogonal vector extends transversely of a boundary surface of the turbid medium. The weighting function is rendered symmetrical by selecting an orthogonal vector which extends, for example perpendicularly to the boundary surface situated at a minimum distance from the selected light path. The effect of the boundary surface on the attenuation coefficient of the voxels for the selected light path can thus be simply corrected.

A next version of a method according to the invention is characterized in that the factorizable function contains a Gaussian function, a width of which is related to a light source distance between a light source of the selected light path and the perpendicular plane and to a product of a length of the selected light path and a predetermined diffusion absorption distance of the turbid medium. Such a Gaussian function is given, for example by the function $$W(x_s, \rho, K) = e^{-\ln 2(\rho/\rho_{1/2}(x_s, K))^2}.$$

This function is factorizable by the choice of $\rho^2 = s^2 + t^2$, in which s and t are the two orthogonal vectors defining the plane perpendicular to the selected light path.

A further version of the method according to the invention is characterized in that a half-value width of the Gaussian function is related to a polynomial of a quotient of the light source distance and the length of the selected light path, the half-value width being substantially zero if the light source distance is equal to the length of the selected light path. The light source distance is defined as the distance from a light source at an end of the selected light path to the shortest connecting line between a voxel and the selected light path. An example of such a function is $$f(x_s) = \rho_{1/2}(\tfrac{1}{2}, K)((4x_s(1-x_s))^n$$

in which $x_s$ is the quotient of the light source distance and the selected light path and n is a rational number. For example, the value ½ can be chosen for n. For this value the normalization is in conformity with the theory of uniform variation of κ in an infinite turbid medium.

The invention also relates to a device for the imaging of objects in a turbid medium, which device includes: a light source for irradiating the turbid medium, a photodetector for measuring the light transported through the turbid medium along different lightpaths from source points at which the light enters the turbid medium to detector points at which the light leaves the turbid medium, and a processing unit for reconstructing an image of the interior of the turbid medium on the basis of the measured intensities, the processing unit also including means for determining an estimated intensity of the light near a detector point of a light path by means of a first combination of predetermined attenuation coefficients of voxels of the turbid medium and a predetermined weighting function which is dependent on a position of the voxel relative to the selected light path, means for determining a difference between the estimated intensity and the measured intensity, and means for determining a next value of the attenuation coefficient of a voxel by means of a second combination of the differences determined for the plurality of light paths. It is further object of the invention to provide a device for the imaging of object in a turbid medium which device reduces the calculation time for reconstruction of images. To this end the device according to the invention is characterized in that the weighting function contains a function which can be factorized to a first and a second orthogonal vector which extend transversely of the selected light path.

BRIEF DESCRIPTION OF THE DRAWING

The above and other, more detailed aspects of the invention will be elucidated hereinafter, by way of example, with reference to the drawing.

In the drawing.

DETAILED DESCRIPTION OF THE PREFERRED EMBODIMENT

Figure 1:
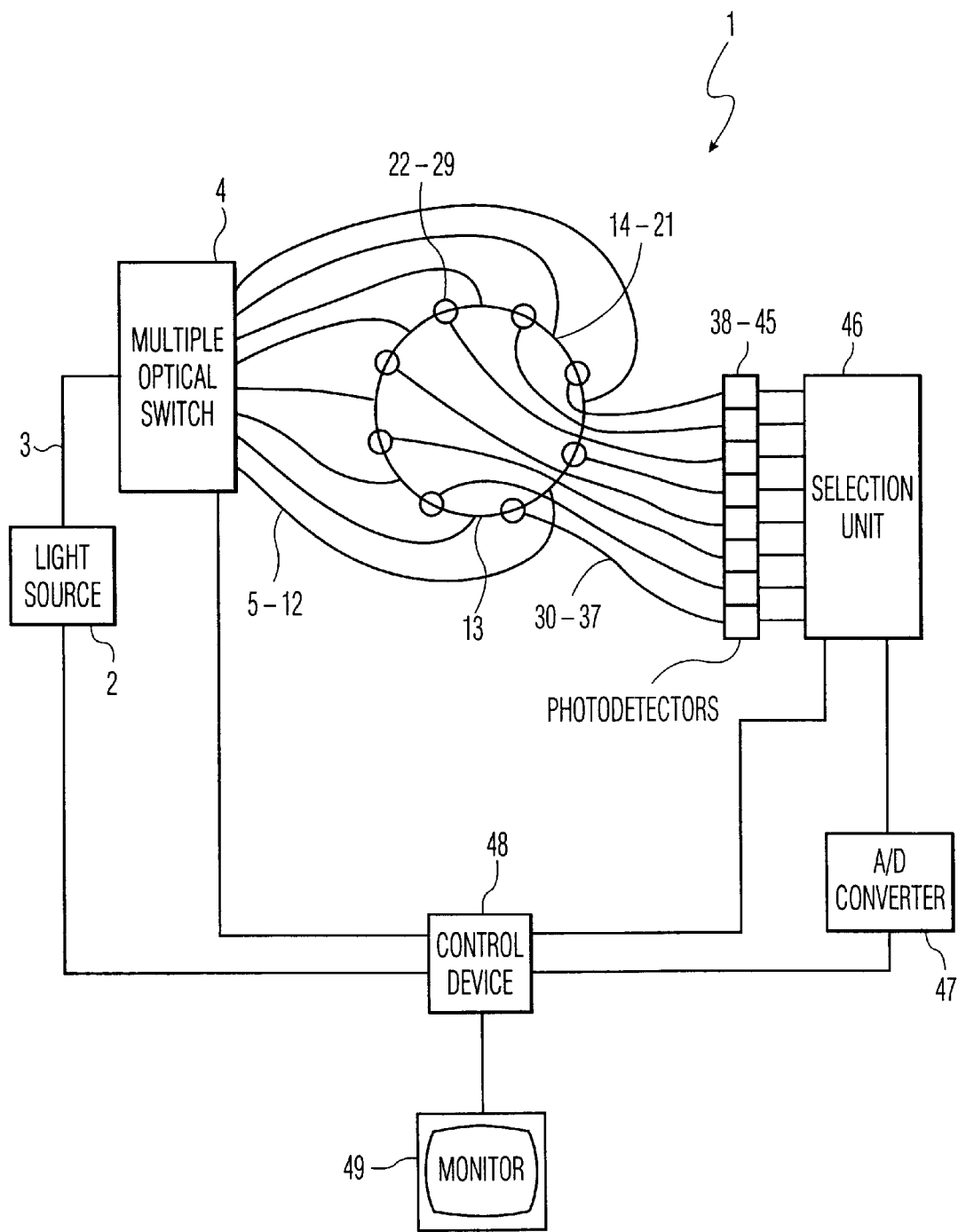
FIG. 1 shows a device for performing measurements on a turbid medium.

FIG. 1 shows an embodiment of a device according to the invention, being an optical mammography device 1 in the present case. Even though the device according to the invention is described, by way of example, as a mammography device, it can also be used for the examination of other parts of a human or animal body. The device described herein is intended for the detection of inhomogeneities in in vivo breast tissue of a part of a breast of a human body. A malignant tumor is an example of such an inhomogeneity. The device according to the invention is arranged to image such anomalies when they are still very small, so that a carcinoma can be detected at an early stage. However, detection takes place without exposing the patient to the risks of examination by means of ionizing radiation, for example X-rays.

The device 1 includes a first plurality of N measuring light sources 14–21, a second plurality of M photodetectors 38–45, and a holder 13. The measuring light sources are mounted in the wall of a holder 13 in positions $r_i$, where i=1 . . . N. The M photodetectors 38–45 are optically coupled to photodetector openings 22–29 in positions $r_j$ in the holder 13, where j=1 . . . M. The numbers N and M are fixed and are valued, for example between 64 and 256. In practice these numbers equal 256 for N as well as M. In FIG. 1 the number of measuring light sources 14–21 and the number of photodetector openings 22–29 are chosen to be equal to eight for the sake of simplicity. The device 1 also includes a light source 2, a first optical light conductor 3, a multiple optical switch 4 and a plurality of optical conductors 5–12. The multiple optical switch 4 connects the light source 1, via the first optical conductor 3 and a second optical conductor, to one of the light transmitting openings 14–21 in the wall of the holder 13, said openings constituting the measuring light sources. The light source 2 used is, for example a semiconductor laser with a wavelength of 810 nm. The measuring device 1 also includes a third plurality of optical conductors 30–37, a selection unit 39, an analog-to-digital converter 47, and a control device 48. The third optical conductors 30–37 are connected, via photodetector openings 22–29 in the wall of the holder 13, to the corresponding number of photodetectors 38–45. The exits of the photodetectors 38–45 are connected, via the selection unit 46, to the analog-to-digital converter 47. The output of the analog-to-digital converter is connected to an input of the control device 48, for example a microcomputer.

In order to reconstruct an image of the interior of a part of the turbid medium, for example a part of the breast of a female, the part of the breast is introduced into the holder 13 of the mammography device 1. Subsequently, the control unit 48 performs intensity measurements for each measuring light source-photodetector pair i,j. In this way intensity measurements are made of light transported through the turbid media along different shortest light paths from sourcepoints at which the light enters the turbid medium to detector points at which the light leaves the turbid medium. Subsequently, the control unit 48 reconstructs an image of the interior of the part of the breast situated within the holder 13. Subsequently, a monitor 49 displays the reconstructed image of the interior of the part of the breast. An iterative method which is known from the cited article "The forward and inverse problems in time resolved infra-red imaging", by S. R. Arridge, published in Medical Optical Tomography, No. IS11, 1993, pp. 35–64, will be explained in detail with reference to FIG. 2.

Figure 2:
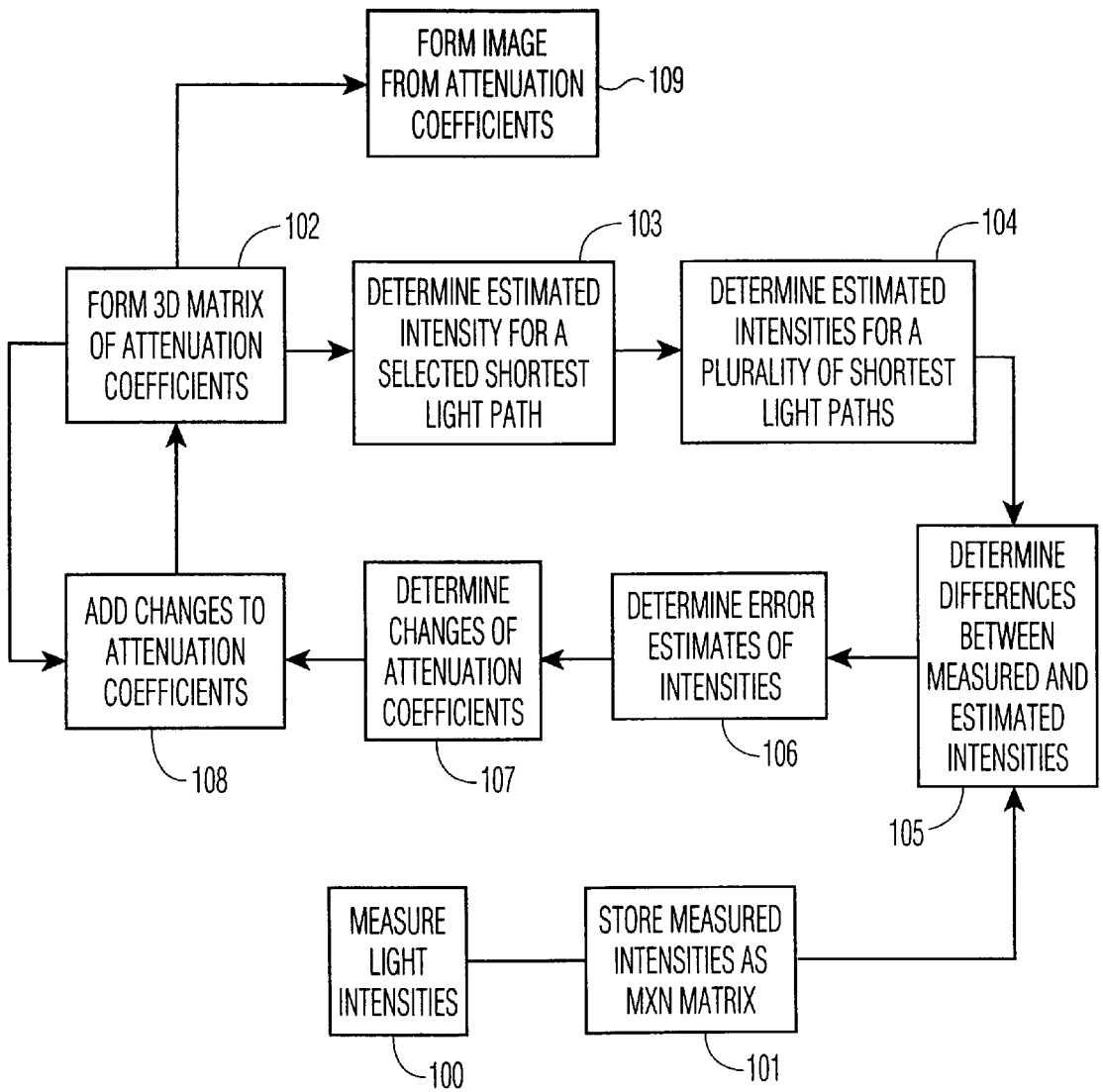
FIG. 2 shows a flow chart of an iterative method for forming an image of a turbid medium.

FIG. 2 shows a flow chart illustrating the known iterative method. During a first step, represented by a first block 100 in FIG. 2, the intensities $I_{i,j}$ of each measuring light source/photodetector pair (i,j) of the holder 13 are measured. During a next step, represented by a second block 101 in FIG. 2, these intensities are stored as a M×N matrix in a memory of the control unit 48. Subsequently, there is chosen an orthogonal system X, Y, Z of voxels which comprises the part of the breast in the holder. With each voxel there is associated an attenuation coefficient $\kappa_{x,y,z}$, which coefficients together constitute a three-dimensional matrix. This is represented by a third block 102 in FIG. 2. During a next step of the method, represented by a fourth block 103 in FIG. 2, a change 61 concerning the estimated intensity $I_s(i,j)$ of the light incident on a photodetector of a measuring light source/photodetector pair i,j of a selected shortest light path is determined from a sum, taken over substantially all voxels present in the part of the breast, of a product of a first function $W_x(x,K)$ and a weighting function $W(x,\rho,K)$, where K is equal to the product of κ and the distance between the measuring light source and a photodetector opening of the selected shortest light path. The function $W_x(x_s,K)$ is determined as:

$$\frac{\Delta K V K_0}{2\pi(1-x_s)x_s} \quad (4)$$

In conformity with the diffusion approximation for an infinite medium, the weighting function $W(x_s,\rho,K)$ is approximated by the formula $$W(x_s, \rho, K) = \frac{\sqrt{(r-x_s)^2 x_s^2}}{(\rho^2 + (r-x_s)^2)(\rho^2 + x_s^2)} e^{-K\left(\sqrt{\rho^2+(r-x_s)^2} + \sqrt{(r^2+x_s^2)}-r\right)} \quad (5)$$

in which $x_s$ is the light source distance of the selected shortest light path, $\rho$ is the distance between the voxel and the selected shortest light path, and K is the product of the attenuation coefficient $\kappa$ and the length of the selected shortest light path. The determination of the distances $\rho$ and $x_s$ will be described with reference to FIG. 3.

Figure 3:
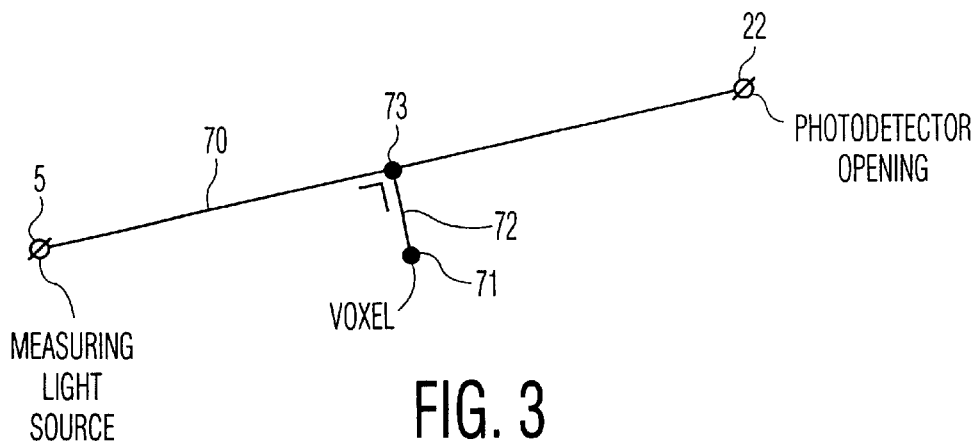
FIG. 3 shows a light path between a measuring light source, a photodetector opening and a voxel.

FIG. 3 shows, by way of example, a measuring light source 5, a photodetector opening 22 and a line 70 which represents the selected shortest light path. The light source distance $x_s$, being the distance between the measuring light source 5 and the shortest connecting line between a voxel 71 and the selected shortest light path 70, is represented by a second line 72. The distance $x_s$ is then determined as the distance between the measuring light source 5 and a point of intersection 73. The distance $\rho$ is determined by the distance from the shortest connecting line between the voxel 71 and the point of intersection 73. In conformity with the method according to the invention, the exponential function in the formula (5), calculated in this step, can be approximated by a Gaussian function, a width of which is related to the light source distance and to a product K of a length of the selected shortest light path and a predetermined diffusion absorption distance of the part of the breast. For example, the function:

$$W_g(x_s, \rho, K) \cong e^{-\ln 2(\rho/\rho_{1/2}(x_s,K))^2} \quad (6)$$

This is a reasonable approximation of the formula (5) for $K \to \infty$. The half-value width of the Gaussian function $W_g$ is related to a polynomial of a quotient of the light source distance and the length of the selected shortest light path, the half-value width becoming substantially equal to zero when the light source distance becomes equal to the length of the selected shortest light path. When relative co-ordinates $x'=x_s/r$ and $\rho'=\rho/r$ are used, the half-value width according to the invention can be chosen in such a manner that $\rho_{1/2}(x', K)=\rho_{1/2}(\frac{1}{2},K)(4x'(1-x'))^n$, where n, for example, equals $\frac{1}{2}$ and $\rho_{(1/2)}(\frac{1}{2},K)$ is approximated by $$\frac{1}{\sqrt{2/\ln(2K+4)}}$$

The Gaussian function $W(x_s,\rho,K)$ can be factorized to, for example a function of $W_g(x_s,s,K)$ and a function $W_g(x_s,t,K)$, where s and t represent two orthogonal vectors which extend transversely to the selected shortest light path, where $\rho^2=s^2+t^2$. This can be written as $W_g(x_s,\rho,K)=W_g(x_s,s,K)W_g(x_s,t,K)$, where $$W_g(x_s,s,K) = e^{-\ln 2(s/\rho_{1/2}(x_s,K))^2} \quad (7)$$

and $$W_g(x_s,t,K) = e^{-\ln 2(t/\rho_{1/2}(x_s,K))^2} \quad (8)$$

The calculation of the change of the intensity of the selected shortest light path, due to the attenuation coefficients of the voxels, will be explained by way of the factorizable function and with reference to the description of FIG. 5. During a next step, represented by a fifth block 104 in FIG. 2, the estimated intensity associated with the first selected shortest light path is determined and subsequently estimated intensities $I_s(i,j)$ are determined for the plurality of shortest light paths i, j. Subsequently, during a next step of the method, represented by a sixth block 105 in FIG. 2, the differences $\delta I(i,j)$ between the measured intensity $I(i,j)$ and the estimated intensity $I_s(i,j)$ are determined per light path. On the basis of the differences $\delta I(i,j)$ determined, an error estimate $I_f(i,j)$ is determined during a next step, represented by a seventh block 106 in FIG. 2. Subsequently, during a next step, represented by an eighth block 107 in FIG. 2, a change of the attenuation factor $\kappa_{x,y,z}$ of the voxels of the part of the breast is determined by backprojection of the error estimate. An example of such a backprojection for determining the change of the attenuation coefficient is $$\delta\kappa_{x,y,z} = \frac{\sum\limits_{i,j=1}^{i,j=N} I_f(i,j)G(x_s, \rho, K)}{\sum\limits_{i,j=1}^{i,j=N} G(x_s, \rho, K)}$$

where $G(x_s,\rho,K)=W(x_s,\rho,K)$ and $I_f(i,j)$ represents the error estimate determined between the estimated intensity and the measured intensity of the plurality of shortest light paths. During a next step of the method, represented by a ninth block 108 in FIG. 2, the changes of the attenuation coefficient $\kappa_{x,y,z}$ are added to the values of $\kappa_{x,y,z}$.

After some iterations, the values $K_{x,y,z}$ will have been sufficiently accurately determined so as to yield an image of the interior of the part of the breast which could be used for diagnostic purposes. To this end, during a next step of the method, represented by a tenth block 109 in FIG. 2, an image is determined from the three-dimensional matrix of attenuation coefficients $\kappa_{x,y,z}$.

In order to reduce the calculation time required to determine the estimated intensity per measuring light source/photodetector pair, a version of the method according to the invention not only utilizes the factorizable function but also optimizes the sequence of determination of the contributions by the voxels to the estimated intensity of a selected shortest light path between a measuring light source/photodetector pair. To this end, for example a first axis of the orthogonal system x, y, z is chosen in such a manner that, relative to the two other axes, this first axis is situated nearest to the selected shortest light path. The selected shortest light path is subsequently approximated by light path voxels in the orthogonal system, so that preferably co-ordinates of two neighboring light path voxels differ by one grid unit of the orthogonal system in the direction of the first axis, a change by one grid unit being made from time to time in co-ordinates in the direction of the other axis in order to follow the selected shortest light path. An approximation of this kind is determined, for example by a Bresenham-like algorithm which is extended to three dimensions. A Bresenham algorithm is known from the cited article "Algorithm for computer control of a digital plotter", by J. E. Bresenham, published in IBM Systems Journal, Vol. 4, No. 1965, pp. 28–30. The approximation of the selected shortest light path by light path voxels will be described in detail with reference to the two-dimensional example shown in FIG. 4.

Figure 4:
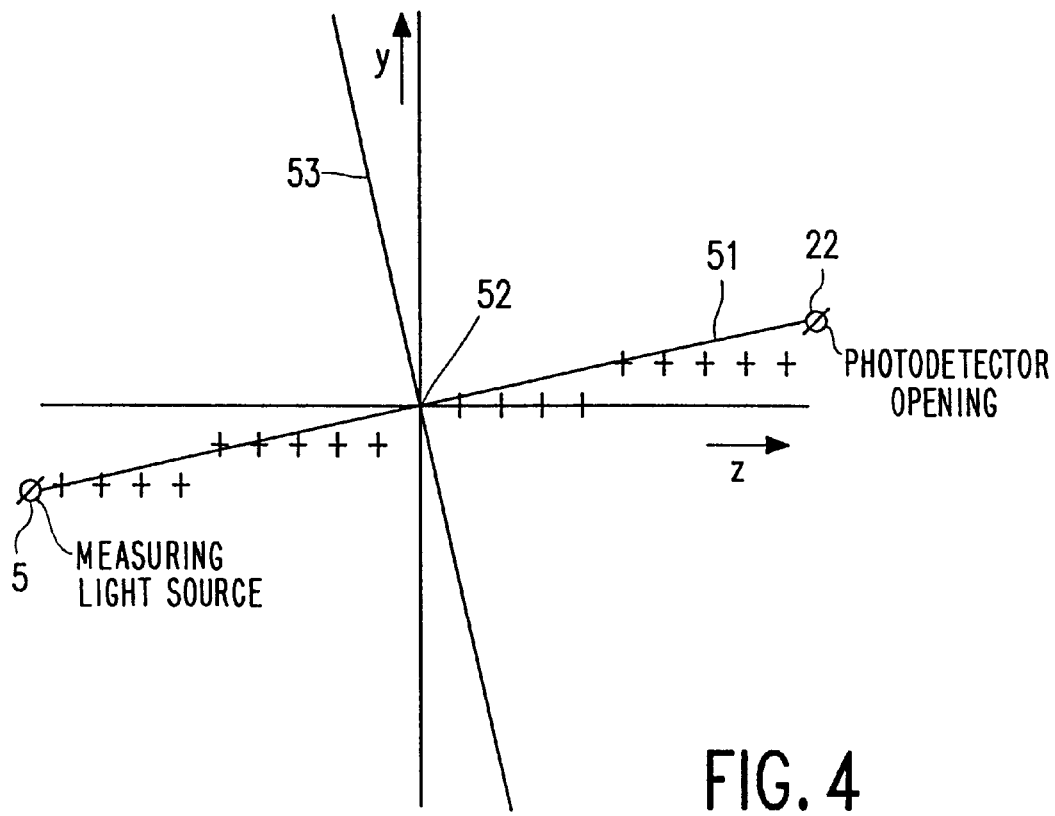
FIG. 4 shows a nearest axis of the orthogonal system relative to a selected shortest light path.

FIG. 4 shows a two-dimensional grid of voxels. The two-dimensional grid also includes a measuring light source 5 and a photodetector 22. The selected shortest light path between the measuring light source 5 and the exit opening 22 is denoted by a line 51. The line 51 is approximated, for example by the voxels 52 which are denoted by the symbol "+" and are referred to hereinafter as light path voxels. In FIG. 4 the axis of the orthogonal system which is situated nearest to the light path is the z axis. The co-ordinates of the indicated light path voxels are determined, for example by means of the known Bresenham algorithm. Subsequently, a plane perpendicular to the selected shortest light path 51 is determined, said plane containing a light path voxel 52 and the two orthogonal vectors s, t. The projection of this plane onto the y, z plane is denoted by a line 53 in FIG. 4.

In order to maintain a symmetrical function which can be split into the functions W(s) and W(t), preferably the first vector s of the two orthogonal vectors is chosen in the direction of the normal to a boundary surface of the part of the breast, said boundary surface being situated at the shortest distance from the selected shortest light path 51. Subsequently, there is determined a second axis of the orthogonal system which is situated nearest to the first orthogonal vector s. Subsequently, in the perpendicular plane a first auxiliary line is chosen which extends parallel to the first orthogonal vector. The first auxiliary line is subsequently approximated by means of first voxels of the orthogonal system. The approximation of the first auxiliary line by the first voxels will be described in detail with reference to the two-dimensional example shown in FIG. 5.

Figure 5:
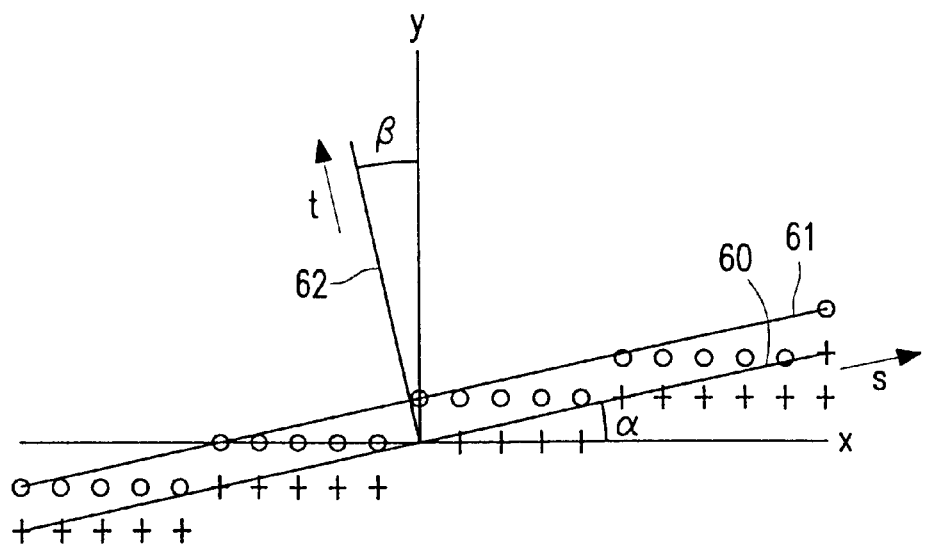
FIG. 5 shows a first and a second auxiliary line in a plane perpendicular to the selected shortest light path.

FIG. 5 shows a two-dimensional grid which contains the second axis and a third axis of the orthogonal grid, for example the x axis and the y axis, respectively. Furthermore, the x axis is situated nearest to the first auxiliary line 60 in FIG. 5. The first auxiliary line 60 is approximated by way of the same Bresenham algorithm as given in the description with reference to FIG. 4. Therefore, in FIG. 5 the differences amount to one grid unit between the co-ordinates in the direction of the x axis of neighboring first voxels approximating the first auxiliary line 60. The voxels approximating the first auxiliary line are denoted by the symbol "+" in FIG. 5.

In order to determine the contributions by the voxels in the perpendicular plane, there is determined a table W[x] whose elements contain contributions of the function $W_g(x_s, s, K)$, $W_g(x_s, s, K)$ being determined by the formule (6). The value of W(s) in a direction of the first orthogonal vector s, represented by the first auxiliary line 60 in FIG. 5, associated with an index x along the x axis in the table W[x], is determined by the function $W(x_s, x/\cos\alpha, K)$, in which the angle $\alpha$ is determined by the first orthogonal vector s and the x axis. The contribution to the intensity by a voxel along the first auxiliary line is subsequently determined by the product $W_g(x_s, s, K) W_g(x_s, t, K)$, in which $W_g(x_s, t, K)$ is determined according to the formule (8). Subsequently, there is determined a first partial sum of the estimated intensity of contributions by the various first voxels whose co-ordinates in the orthogonal system approximate the first auxiliary line 60 in the perpendicular plane 53 (FIG. 4). Furthermore, in this version of the method according to the invention there is preferably determined a second partial sum of the estimated intensity of contributions by different second voxels approximating a second auxiliary line 61, in the perpendicular plane, which extends parallel to the first auxiliary line 60, co-ordinates of the second voxels in the direction of the y axis differing by one grid unit from the corresponding co-ordinates of the first voxels. The second voxels are denoted by the symbol "0" in FIG. 5. The contribution to the estimated intensity by a second voxel is given by the product of $W_g(x_s, t, K)$ and a combination of elements of the table W[x], the value of the function $W_g(x_s, t, K)$ in the direction of the second orthogonal vector t, denoted by a third auxiliary line 62 in FIG. 5, being determined by $W_g(x_s, y/\cos\beta, K)$ in which the angle $\beta$ is determined by the second orthogonal vector t and the y axis. In this case the value of W(s) is determined by a combination of elements in the table W[x], for example, a first-order interpolation given by $(1-\cos\alpha\sin\beta)W[x]+\cos\alpha\sin\beta W[x+1]$.

Furthermore, the previously described step for determining the partial sum for the various voxels on the second line 61 in the selected perpendicular plane 51 is repeated until all contributions to the estimated intensities by substantially all voxels in the perpendicular plane have been determined.

In order to determine the contribution to the intensity by substantially all voxels of the part of the breast, in the version of the method according to the invention said steps are repeated so as to determine partial sums of the voxels for successive perpendicular planes along the selected shortest light path containing the respective light path voxels. To this end, preferably a next perpendicular plane is determined along the selected shortest light path 51, said next perpendicular plane extending parallel to the first perpendicular plane selected. A first auxiliary line in the next perpendicular plane is then given, for example by adding one grid unit to the co-ordinates of the first auxiliary line 60 in the z direction.

It has been found in practice that it is not necessary to determine the contribution to the estimated intensity by a voxel for all voxels in a perpendicular plane, because a voxel which is situated at a large distance from the selected shortest light path makes only a negligibly small contribution. In practice, only 60,000 voxels are used and a minimum distance of approximately 2.66 mm is chosen as the distance between a voxel and the selected shortest light path; the contribution by the voxel to the partial sum can be ignored beyond this distance.

All references cited herein are incorporated herein by reference in their entirety and for all purposes to the same extent as if each individual publication or patent or patent application was specifically and individually indicated to be incorporated by reference in its entirety for all purposes.

I claim:

1. A method of localizing an object in a turbid medium, which method includes the following steps:
   irradiating the turbid medium and determining an intensity of a part of the light transported through the turbid medium along a plurality of light paths,
   determining an estimated intensity of the light of a selected light path by way of a first combination of predetermined attenuation coefficients of voxels of the turbid medium and a predetermined weighting function which is related to a position of a voxel relative to the selected light path,
   determining a difference between the estimated intensity and the determined intensity for the selected light path, and
   determining a next value of the attenuation coefficients of the voxels by way of a second combination of the differences determined for the plurality of light paths from source points at which the light enters the turbid medium to detector points at which the light leaves the turbid medium, characterized in that the weighting function is determined in such a manner that it contains a function which can be factored along a first and a second orthogonal vector which extend transversely to the selected light path.

2. A method as claimed in claim 1, characterized in that the method also includes the following steps for determining the estimated intensity for the selected light path:
   selecting a first axis of an orthogonal system which corresponds best to the direction of the selected light path, approximating the selected light path in the turbid medium by light path voxels, determining a plane perpendicular to the selected light path, said perpendicular plane being determined by a light path voxel and the first and the second orthogonal vector, approximating a first auxiliary line in the perpendicular plane which is oriented substantially parallel to the first orthogonal vector by first voxels, determining a table of a function W(s), dependent on the first orthogonal vector, whose elements contain contributions of W(s) which are dependent on the distance between one of the first voxels and the selected light path, and determining a partial sum of the estimated intensity of contributions by various first voxels as a product of a function W(t) which is dependent on the second orthogonal vector and elements of W(s).

3. A method as claimed in claim 2, characterized in that, for the approximation of the first auxiliary line, two neighboring first voxels are determined in such a manner that associated co-ordinates differ by one grid unit in a direction of a second axis of the orthogonal system, which is situated nearest to the first orthogonal vector.

4. A method as claimed in claim 2, characterized in that the method includes a step in which a second auxiliary line in the perpendicular plane, being directed substantially parallel to the first auxiliary line, is approximated by second voxels in such a manner that, in a direction of a third axis of the orthogonal system, co-ordinates of the second voxels differ by one grid unit from corresponding co-ordinates of the first voxels, the partial sum of the estimated intensity being determined from the contribution by different second voxels.

5. A method as claimed in claim 2, characterized in that, for the approximation of the selected light path, co-ordinates of two neighboring light path voxels differ by one grid unit in a direction of the first axis.

6. A method as claimed in claim 2, characterized in that the first or the second orthogonal vector extends transversely to a boundary surface of the turbid medium.

7. A method as claimed in claim 1, characterized in that the factorable function contains a Gaussian function, a width of which is related to a light source distance between a light source of the selected light path and the perpendicular plane and to a product of a length of the selected light path and a predetermined diffusion absorption distance of the turbid medium.

8. A method as claimed in claim 7, characterized in that a half-value width of the Gaussian function is related to a polynomial of a quotient of the light source distance and the length of the selected light path, the half-value width being substantially equal to zero if the light source distance is equal to the length of the selected light path.

9. A device for the imaging of objects in a turbid medium, which device includes:

a light source for irradiating the turbid medium, a photodetector for measuring the light transported through the turbid medium along different lightpaths from source points at which the light enters the turbid medium to detector points at which the light leaves the turbid medium and a processing unit for reconstructing an image of the interior of the turbid medium on the basis of the measured intensities, the processing unit also including means for determining an estimated intensity of the light near a detector point of a light path by means of a first combination of predetermined attenuation coefficients of voxels of the turbid medium and a predetermined weighting function which is dependent on a position of the voxel relative to the selected light path, means for determining a difference between the estimated intensity and the measured intensity, and means for determining a next value of the attenuation coefficient of a voxel by means of a second combination of the differences determined for the plurality of light paths, characterized in that the weighting function contains a function which can be factored along a first and a second orthogonal vector which extend transversely to the selected light path.

10. The method of claim 1 further including one or more repetitions of the steps of determining an estimated intensity, determining a difference between the estimated intensity and the determined intensity, and determining a next value of the attenuation coefficients.

11. The method of claim 10 further comprising, after the one or more repetitions, a step of determining an image of the object in the turbid medium from the values of the attenuation coefficients.

* * * * *